United States Patent
Yan et al.

(10) Patent No.: US 9,170,187 B2
(45) Date of Patent: Oct. 27, 2015

(54) FLOW CYTOMETER AND FLUIDIC SYSTEM THEREOF

(71) Applicants: SHENZHEN MINDRAY BIO-MEDICAL ELECTRONICS CO., LTD., Shenzhen (CN); BEIJING SHEN MINDRAY MEDICAL ELECTRONICS TECHNOLOGY RESEARCH INSTITUTE CO., LTD., Haidan District Beijing (CN)

(72) Inventors: Baohua Yan, Haidian District Beijing (CN); Chuixin Liao, Haidian District Beijing (CN); William Li, Haidian District Beijing (CN); Huawen Yan, Haidian District Beijing (CN); Wenheng Guo, Haidian District Beijing (CN)

(73) Assignees: SHENZHEN MINDRAY BIO-MEDICAL ELECTRONICS CO., LTD., Shenzhen (CN); BEIJING SHEN MINDRAY MEDICAL ELECTRONICS TECHNOLOGY RESEARCH INSTITUTE CO., LTD., Beijing (CN)

( * ) Notice: Subject to any disclaimer, the term of this patent is extended or adjusted under 35 U.S.C. 154(b) by 0 days.

(21) Appl. No.: 14/618,931

(22) Filed: Feb. 10, 2015

(65) Prior Publication Data

US 2015/0153263 A1 Jun. 4, 2015

Related U.S. Application Data

(63) Continuation of application No. PCT/CN2013/074592, filed on Apr. 24, 2013.

(30) Foreign Application Priority Data

Aug. 10, 2012 (CN) .......................... 2012 1 0284806

(51) Int. Cl.
*G01N 1/00* (2006.01)
*G01N 15/14* (2006.01)
*G01N 1/10* (2006.01)
*G01N 15/10* (2006.01)

(52) U.S. Cl.
CPC .............. *G01N 15/1404* (2013.01); *G01N 1/10* (2013.01); *G01N 15/1434* (2013.01); *G01N 2015/1006* (2013.01); *G01N 2015/1409* (2013.01); *G01N 2015/1486* (2013.01)

(58) Field of Classification Search
CPC ................ G01N 1/2813; G01N 1/286; G01N 2001/284; G01N 1/2806; G02B 21/32
USPC ............................................ 356/36, 300–445
See application file for complete search history.

(56) References Cited

U.S. PATENT DOCUMENTS

| | | | |
|---|---|---|---|
| 5,245,318 A | 9/1993 | Tohge et al. | |
| 5,395,588 A | 3/1995 | North, Jr. et al. | |
| 7,776,268 B2 * | 8/2010 | Rich | 422/81 |
| 2008/0092961 A1 | 4/2008 | Bair et al. | |
| 2008/0106736 A1 * | 5/2008 | Graves et al. | 356/338 |

FOREIGN PATENT DOCUMENTS

| | | |
|---|---|---|
| CN | 101236149 A | 8/2008 |
| JP | 3499009 B2 | 2/2004 |

* cited by examiner

*Primary Examiner* — Abdullahi Nur
(74) *Attorney, Agent, or Firm* — Kory D. Christensen; Stoel Rives LLP

(57) ABSTRACT

A flow cytometer and a fluid system are provided. The fluid system comprises a flow cell, a sample providing unit, a waste container, a sheath container, a negative pressure source, a quantitative unit and a sample flow monitoring unit, the negative pressure source, the waste container and the flow cell are connected, a negative pressure source, which provides a negative pressure relative to the sample providing unit for the flow cell so that the sample providing unit causes the sample to flow into the flow cell under the negative pressure, a sample flow monitoring unit monitors a flow of the sample fluid transported from the sample providing unit to the flow cell and outputs a feedback signal reflecting flow changes of the sample fluid in real-time; wherein the controller receives the feedback signal and controls the quantitative unit to adjust a flow of the sheath fluid according to the feedback signal.

8 Claims, 1 Drawing Sheet

FLOW CYTOMETER AND FLUIDIC SYSTEM THEREOF

TECHNICAL FILED

This disclosure relates generally to particle analysis, and more specifically to a flow cytometer and a fluidic system.

BRIEF SUMMARY

The present disclosure relates to a flow cytometer and a fluidic system, which uses an absolute count function, but neither adds standard particles nor pumps and pushes a sample by a metering pump repeatedly.

In one aspect of the present disclosure, a flow cytometer is provided that includes a controller, a fluidic system for providing a sample fluid and a sheath fluid and collecting a waste fluid produced after a test, and an optical detection system for illuminating a sample fluid and acquiring information when the sample fluid passes through a light beam of illumination. In one embodiment, the fluidic system includes a flow cell, which contains the sample fluid surrounded by the sheath fluid and provides a region where the sample fluid is illuminated; a sample providing unit, which connects with the flow cell and draws a sample from a sample tube; a waste container, which connects with the flow cell and collects the waste fluid flowing from the flow cell; a negative pressure source, which provides a negative pressure relative to the sample providing unit for the flow cell so that the sample providing unit causes the sample to flow into the flow cell under the negative pressure; a sheath container, which connects with the flow cell and transports the sheath fluid to the flow cell; a quantitative unit, which is set on a pipeline between the sheath container and the flow cell, and acquires the sheath fluid from the sheath container and transports the sheath fluid to the flow cell according to a setting flow of the sheath fluid; a sample flow monitoring unit, which monitors a flow of the sample fluid transported from the sample providing unit to the flow cell and outputs a feedback signal reflecting flow changes of the sample fluid in real-time. The controller may receive the feedback signal and control the quantitative unit to adjust a flow of the sheath fluid according to the feedback signal.

In another aspect of the present disclosure, a fluidic system of the flow cytometer is provided that comprises a flow cell, which contains a sample fluid surrounded by a sheath fluid and provides a region where the sample fluid is illuminated; a sample providing unit, which connects with the flow cell and draws a sample from a sample tube; a waste container, which connects with the flow cell and collects the waste fluid flowing from the flow cell; a negative pressure source, which provides a negative pressure for the flow cell relative to the sample providing unit so that the sample providing unit causes the sample to flow into the flow cell under the negative pressure; a sheath container, which connects with the flow cell and transports the sheath fluid to the flow cell; a quantitative unit, which is set on a pipeline between the sheath container and the flow cell and acquires the sheath fluid from the sheath container and transports the sheath fluid to the flow cell according to a setting flow of the sheath fluid; a sample flow monitoring unit, which monitors a flow of the sample fluid transported from the sample providing unit to the flow cell and outputs a feedback signal reflecting flow changes of the sample fluid in real-time. The quantitative unit may adjust the flow of sheath fluid according to the feedback signal.

DETAILED DESCRIPTION

Figure 1:
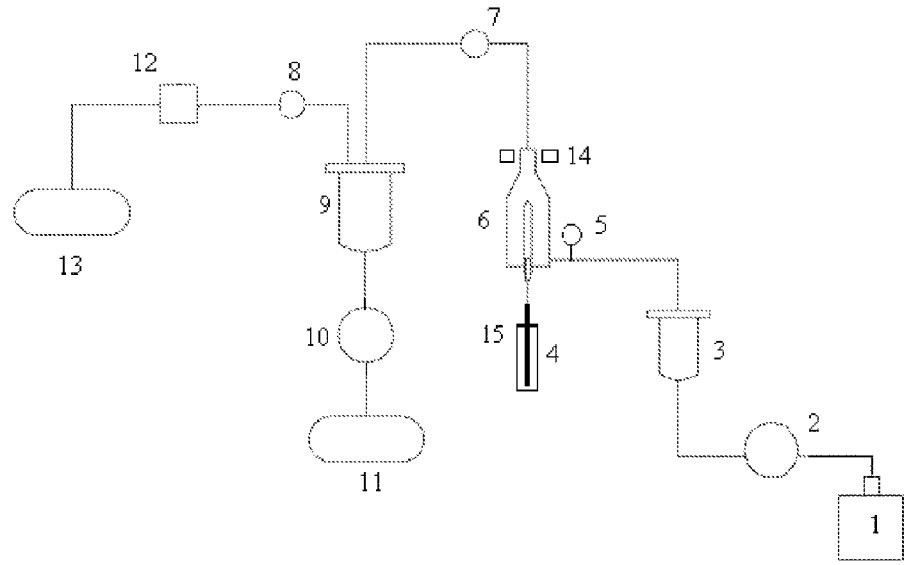
FIG. 1 is a schematic drawing of a fluidic system.

A flow cytometer is often used for analysis and statistics of small particles. In the medical filed, it is especially used for classifying and counting cells. Typically, a user needs to determine the total amount of cells collected. However, the user may also need the concentration of the cells collected in some cases. Accordingly, the flow cytometer needs an absolute count for part of the cells collected so as to obtain the concentration of the cells collected, and needs a non-absolute count (common measure) of most of the remaining cells collected so as to the obtain total amount of the cells collected.

In order to determine the total amount of the cells collected and make an absolute count, conventional flow cytometers have two options. One option is measurement method using absolute volume. Another option is a measurement method of adding standard particles of a known concentration.

For the measurement method based on absolute volume, a quantitative component of a flow cytometer may be used. For example, a metering pump, may be used for testing a sample volume, after which a concentration of cells collected is calculated by dividing the total amount of the cells collected by the sample volume so as to realize the absolute count.

For a measurement method of adding standard particles of a known concentration, a flow cytometer does not have the quantitative component. When a user needs an absolute count for a sample, standard particles of known concentration are added to the sample. This method mixes standard particles of known concentration with the sample of known volume, after which the concentration of standard particles in a mixing liquid which is formed after mixing can be calculated. The flow cytometer tests the total amount of the standard particles and total amount of the collecting cells in the mixing liquid, after which a mixing liquid volume may be calculated according to the total amount of standard particles, and then the concentration of the sample could be calculated by dividing the total amount of the collecting cells by the mixing liquid volume so as to achieve an absolute count. This method calculates the sample volume by adding the standard particles of known concentration, which needs the user to precisely input the standard particles with known concentration. This method places high requirements on users, making operation thereof inconvenient an increasing costs. However, in a measurement method based on absolute volume, the metering pump pushes samples quickly, and a volume is limited for every push, in order to meet the total amount requirement of the collecting sample, so the flow cytometer usually pushes the samples several times when testing the samples, and the metering pump needs to pump the sample and then push the sample every time. Thus, measurement is interrupted, and measurement time is extended.

Absolute count means a test for acquiring the concentration of cells collected, which test needs to acquire a number of the cells collected and a sample volume. In the present embodiment, flow of a sample fluid could be quantified precisely, and then an absolute count can be realized according to the sample volume which is calculated by the flow of sample fluid and time. The present embodiment realizes an absolute count without adding standard particles or acquiring sample volume with a quantifying device, but can test the sample continually with a continuous and stable sample fluid. The problem of measurement interruption and low efficiency caused by pumping and pushing the sample repeatedly does not exist.

In the present embodiment, the continuous and stable sample fluid is realized by forming a stable negative pressure relative to a sample providing unit in a flow chamber, that is, the sample flowing into the flow chamber is motivated by the negative pressure of the flow chamber relative to the sample providing unit. The present negative pressure does not mean atmospheric pressure specifically, but a relative negative pressure. In other words, when pressure in space A is lower than pressure in space B, it means space A has a negative pressure relative to the space B. The pressure value of space A and B can be both higher than atmospheric pressure or can be both lower than atmospheric pressure. If the negative pressure of the flow chamber relative to the sample providing unit is steady, then flow of sample fluid will remain unchanged. The sample volume can be calculated by the flow of sample fluid multiplied by the test time. The collecting cells concentration is calculated by dividing the number of the collecting cells in this period by the sample volume.

According to the principle above, a flow cytometer includes a fluidic system, an optical detection system and a controller, a fluidic system for providing a sample fluid and a sheath fluid and collecting a waste fluid produced after a test, and an optical detection system for illuminating a sample fluid and acquiring information when the sample fluid passing through a light beam of illumination. In one embodiment, the controller controls instrument actions.

As shown in FIG. 1, one embodiment of a fluidic system includes a flow cell 6, a sample providing unit, a sample flow monitoring unit, a sheath unit, a waste unit and a negative pressure source 13. The flow cell 6 contains sample fluid surrounded by the sheath fluid and provides a region where the sample fluid is illuminated. The sample providing unit connects to the flow cell 6 and draws a sample from a sample tube. The sheath unit connects to the flow cell and steadily transports a certain amount of the sheath fluid to the flow cell. The sample fluid surrounds the sheath fluid and forms a steady sample fluid. The waste unit connects to the flow cell and collects a waste fluid flowing from the flow cell during detection. The negative pressure source 13 provides power for the flow cell relative to the sample providing unit and makes pressure of the flow cell lower than the sample providing unit so that provides power for sample flowing into the flow cell. The sample fluid monitoring unit monitors a flow of sample fluid transported from the sample providing unit to the flow cell and outputs in real time a feedback signal reflecting flow changes of the sample fluid. The optical detection system 14 may be arranged on two opposite sides of the flow cell 6, emitting light to the sample and receiving an optical signal after the sample is illuminated.

The sample providing unit can be a sample probe, one end of the sample probe 15 connecting to the flow cell 6 and the other end of the sample probe connecting to a sample tube 4. The flow cell 6 may have an aperture, and the sheath fluid surrounds the sample fluid and passes through the aperture.

In one embodiment, a waste unit includes a waste container 9, which connects with a flow cell 6 by a pipeline and receives a waste fluid flowing from the flow cell, a negative pressure source 13, which connects to a waste container 9 and provides a negative pressure for the waste container relative to the flow cell 6. A pressure of the waste container 9 is lower than the pressure of the flow cell 6, such that the waste fluid flows from the flow cell to the waste container. A negative pressure relative to an aspirating end of a sample probe 15 is formed in the flow cell 6 after the negative pressure provided by a negative pressure source 13 counteracts pressure loss, which is formed when the waste fluid flows out of the flow cell, and then the sample probe 15 draws a sample from a sample tube 4 under the negative pressure and transports the sample to the flow cell 6. In one embodiment, a waste unit also includes a waste pump 10 and a waste tank 11. When the waste container 9 is full of the waste fluid or the waste fluid collected by the waste container arrives at a certain amount, the waste pump 10 pumps the waste fluid from the waste container 9 and draws the waste fluid to the waste tank 11. The negative pressure of the waste container can be provided by the waste pump. The waste pump pumps the waste fluid from the waste container and causes the waste container to have a negative pressure relative to the flow cell 6 before testing, after which the waste pump causes the waste fluid of the waste container to be continually discharged, so the negative pressure of the waste container maintains constant during testing. In another embodiment, a waste unit also includes a negative pressure regulating valve 12, a first control valve 8 and a second control valve 7. The negative pressure regulating valve 12 is disposed on the pipeline between a negative pressure source 13 and a waste container 9. The negative pressure regulating valve regulates a negative pressure of the waste container. The first control valve 8 is set on the pipeline between the negative pressure regulating valve 12 and the waste container 9. The second control valve 7 is set on the pipeline between the waste container 9 and the flow cell 6. The first control valve 8 and the second control valve 7 are controlled by a switch by a controller (not show). The first control valve 8 and the second control valve 7 can be an electromagnetic valve or other valve which is electronically controlled. The first control valve 8 and the second control valve 7 also can be controlled by manually.

A sheath unit may include a sheath container 1 and a quantitative unit 2. The sheath container connects to a flow cell 6 by pipeline. The quantitative unit 2 is set on the pipeline between the sheath container and the flow cell 6. The quantitative unit 2 draws the sheath fluid from the sheath container 1 and transports the sheath fluid to the flow cell 6 according to a setting sheath flow. The quantitative unit 2 can be a metering pump or other device whose transport amount is known. A metering pump can quantify the fluid exactly and rotate continuously.

A sample flow monitoring unit monitors a flow of sample fluid transported from the sample providing unit to the flow cell and outputs a feedback signal reflecting flow changes of the sample fluid. The quantitative unit adjusts the outputting sheath flow according to the feedback signal. In the present embodiment, the sample flow monitoring unit can be a pressure sensor 5. The pressure sensor 5 is nearby the flow cell 6 for testing the pressure of the flow cell and outputting a pressure feedback signal. For example, the pressure sensor 5 can be fixed to the flow cell 6 (e.g., wall, entrance or exit of the flow cell) or some place around the flow cell 6. To increase the accuracy of a test pressure value, the pressure sensor 5 may be as close as possible to the flow cell 6.

The controller connects with the control valves (7, 8), the quantitative unit 2, and the pressure sensor 5 by a wired or wireless mode. The pressure sensor 5 transmits a pressure feedback signal (that is test pressure value) to the controller. The controller controls the quantitative unit to adjust a flow of sheath fluid according to the pressure feedback signal.

Precise counting requires the flow of sample fluid be maintained constant during testing. A negative pressure of a flow cell 6 maintains constant relative to a sample providing unit, and a negative pressure of the flow cell 6 can be tested by a pressure sensor 5. A negative pressure of the waste container maintains constant while testing. If the negative pressure of the flow cell 6 changes, then the flow of the quantitative unit is adjusted to change the pressure loss, which is formed when the waste fluid passes through the flow cell 6, so as to cause the negative pressure of the flow cell 6 to be constantly maintained.

Figure 2:
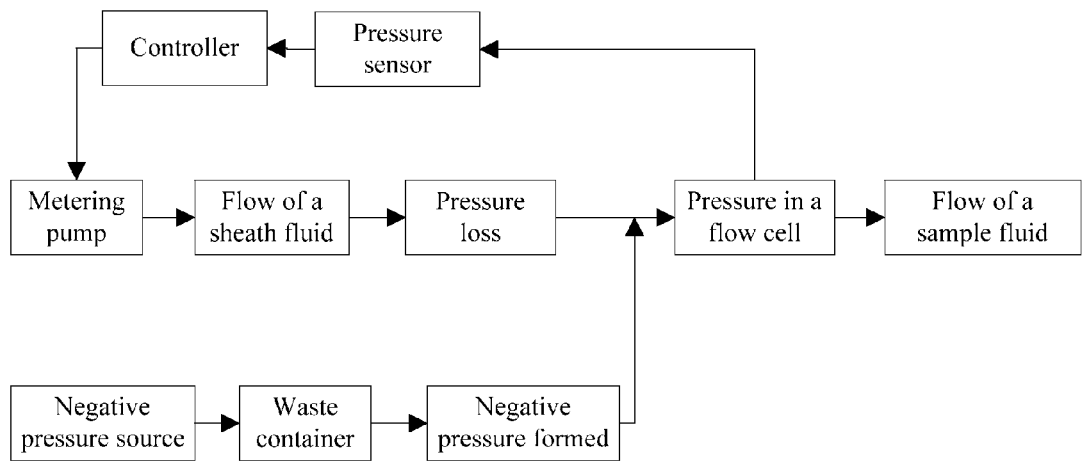
FIG. 2 is flow diagram for a control system.

FIG. 2 illustrates a control process according to one embodiment of the present disclosure. A negative pressure source produces a negative pressure above a fluid surface of a waste container. A negative pressure is maintained in a flow cell after the negative pressure of the waste container counteracts a pressure loss, which is formed when the waste fluid flows out of the flow cell. A sample flows into the flow cell by the negative pressure formed in the flow cell. The negative pressure of the flow cell is different from the negative pressure of the waste container. The negative pressure of the flow cell will be affected by the sum of the flow of the sample fluid and the flow of the sheath fluid. Because the sheath fluid flowing to the flow cell is not drawn by the power of the negative pressure, the negative pressure changes of the flow cell will not affect the sheath flow, but the negative pressure changes of the flow cell will affect the flow of sample fluid. The pressure value of the flow cell is tested by a pressure sensor. The pressure sensor transmits the pressure value to the controller. The controller adjusts a setting flow of the sheath fluid set by the quantitative unit according to the pressure value and changes a pressure loss caused by sum of the flow of sample fluid and the flow of the sheath fluid. The pressure of the flow cell is maintained constant. As the pressure sensor tests that the negative pressure of the flow cell decreases, the quantitative unit of the sheath fluid decreases the flow of the sheath fluid. As the pressure sensor tests that the negative pressure of the flow cell increases, the quantitative unit of the sheath fluid increases the flow of the sheath fluid. This control process could be realized by a PID controller or other means.

The following illustrates a flow of the present embodiment.

(1) Detection flow. At the beginning of testing, a quantitative unit 2 is turned on. A control valve 7 and a control valve 8 are turned on synchronously. The quantitative unit 2 transports the sheath fluid to a flow cell 6. A waste container 9 has a constant negative pressure and provides power for waste fluid flowing out of the flow cell 6, after which a negative pressure is maintained in a flow cell after the negative pressure of the waste container counteracts a pressure loss, which is formed when the waste fluid flows out of the flow cell. A sample flows into the flow cell by the negative pressure formed in the flow cell. After the sample is drawn into the flow cell, the sample surrounded by the sheath fluid flows out of the flow cell, which is ultimately collected in the waste container 9. An optical system 14 detects information relating to the sample fluid passing through the flow cell 6, e.g., FSC signal, SSC signal and/or FL signal of the sample are acquired, after which the signals are processed and calculated, and a detection result is finally outputted.

(2) Waste fluid discharge flow. After detection, the quantitative unit 2 is turned off. The control valve 7 and the control valve 8 are turned off synchronously, after which a waste pump 10 is turned on to discharge the waste fluid of the waste container out of the instrument. The waste pump 10 is turned off after the waste fluid is discharged, after which the first control valve 8 is turned on to cause the negative pressure of the waste container to arrive at a pressure set by a negative pressure valve 12.

In the present embodiment, the negative pressure is formed in the flow cell by the negative pressure source, and the sample is drawn to the flow cell motivated by the negative pressure. By a pressure sensor monitoring the pressure of the flow cell, the flow of the sheath fluid is controlled according to a feedback of a monitoring result. The flow cell maintains a constant pressure, and the sample maintains a constant flow, so the sample can be tested continuously. A sample volume can be calculated according to the flow of sample fluid and test time after testing, after which the concentration information of the test particles can be calculated by dividing the collecting particles by the sample volume so as to realize an absolute count. The present embodiment realizes an absolute count without adding standard particles or acquiring sample volume with quantifying device.

In another embodiment, a negative source 13 could also connect to a flow cell 6 directly and provide a negative pressure to the flow cell 6, which causes the pressure of the flow cell 6 to be lower than an aspirating end of a sample probe 15.

In another embodiment, as show in FIG. 1, a sheath unit includes a sheath fluid container 1, a quantitative unit 2, and a pulse eliminator 3. The quantitative unit 2 can be a metering pump. The pulse eliminator 3 reduces or eliminates pressure fluctuation. The pulse eliminator 3 may be set on a pipeline between the metering pump and a flow cell 6. The pulse eliminator 3 reduces or eliminates pressure waves while the metering pump is working.

The sample flow monitoring unit can also be a flow sensor in another embodiment. The flow sensor is set on a tube between a sample providing unit and a flow cell and a output end of the flow sensor connects to a controller. The flow sensor tests a flow of sample fluid directly and transmits a flow feedback signal acquired by the flow sensor to the controller. The controller controls a quantitative unit, adjusting a flow of a sheath fluid according to the feedback signal so as to maintain the flow of the sample fluid be constant during detection. The flow sensor can test the flow of the sample fluid more directly comparing with the pressure sensor, so as to maintain the flow of the sample fluid be constant during testing.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A flow cytometer, comprising a controller, a fluidic system for providing a sample fluid and a sheath fluid and collecting a waste fluid produced after a test, and an optical detection system for illuminating the sample fluid and acquiring information when the sample fluid passes through a light beam of illumination, wherein the fluidic system comprises:
a flow cell, which contains the sample fluid surrounded by the sheath fluid and provides a region where the sample fluid is illuminated;
a sample providing unit, which connects with the flow cell and draws a sample from a sample tube;
a waste container, which connects with the flow cell and collects the waste fluid flowing from the flow cell;
a negative pressure source, which provides a negative pressure for the flow cell relative to the sample providing unit so that the sample providing unit causes the sample to flow into the flow cell under the negative pressure;
a sheath container, which connects with the flow cell and transports the sheath fluid to the flow cell;
a quantitative unit, which is set on a pipeline between the sheath container and the flow cell, and acquires the sheath fluid from the sheath container and transports the sheath fluid to the flow cell according to a setting flow of the sheath fluid; and
a sample flow monitoring unit, which monitors a flow of the sample fluid transported from the sample providing unit to the flow cell and outputs a feedback signal reflecting flow changes of the sample fluid in real-time;
wherein the controller receives the feedback signal and controls the quantitative unit to adjust a flow of the sheath fluid according to the feedback signal to maintain the flow of the sample fluid substantially constant;
wherein the sample flow monitoring unit is a pressure sensor, which is nearby the flow cell and capable of monitoring a pressure of the flow cell; the pressure sensor connects with the controller and outputs a pressure feedback signal to the controller; the controller controls the quantitative unit to increase the flow of the sheath fluid when the pressure sensor monitors that the pressure of the flow cell increases, and to decrease the flow of the sheath fluid when the pressure sensor monitors that the pressure of the flow cell decreases;
or
the flow monitoring unit is a flow sensor, which is set on a pipeline between the sample providing unit and the flow cell and is capable of monitoring the flow of the sample fluid; the flow sensor connects to the controller and outputs a flow feedback signal to the controller; the controller controls the quantitative unit to increase the flow of the sheath fluid when the flow sensor monitors that the flow of the sample fluid increases, and to decrease the flow of the sheath fluid when the flow sensor monitors that the flow of the sample fluid decreases.

2. The flow cytometer according to claim 1, wherein the negative pressure source further connects to the waste container and provides a negative pressure to cause the waste fluid to flow from the flow cell to the waste container, and a negative pressure of the flow cell relative to the sample providing unit is maintained after the negative pressure provided by the negative pressure source counteracts a pressure loss which is formed when the waste fluid flows out of the flow cell.

3. The flow cytometer according to claim 1, further comprising a negative pressure regulating valve, a first control valve and a second control valve, wherein the negative pressure regulating valve is set on a pipeline between the negative pressure source and the waste container for regulating the negative pressure of the waste container, the first control valve is set on a pipeline between the negative pressure regulating valve and the waste container, the second control valve is set on a pipeline between the waste container and the flow cell, and the first control valve and the second control valve are controlled to switch between on and off by the controller.

4. The flow cytometer according to claim 1, wherein the quantitative unit is a metering pump, the flow cytometer further comprises a pulse eliminator for reducing or eliminating pressure fluctuation, and the pulse eliminator is set on a pipeline between the quantitative unit and the flow cell.

5. A fluidic system of a flow cytometer, comprising:
a flow cell, which contains a sample fluid surrounded by a sheath fluid and provides a region where the sample fluid is illuminated;

a sample providing unit, which connects with a flow cell and draws a sample from a sample tube;

a waste container, which connects with the flow cell and collects a waste fluid flowing from the flow cell;

a negative pressure source, which provides a negative pressure for the flow cell relative to the sample providing unit so that the sample providing unit causes the sample to flow into the flow cell under the negative pressure;

a sheath container, which connects with the flow cell and transports the sheath fluid to the flow cell;

a quantitative unit, which is set on a pipeline between the sheath container and the flow cell, and acquires the sheath fluid from the sheath container and transports the sheath fluid to the flow cell according to a setting flow of sheath fluid; and a sample flow monitoring unit, which monitors a flow of sample fluid transported from the sample providing unit to the flow cell and outputs a feedback signal reflecting flow changes of sample fluid in real-time;

wherein the quantitative unit adjusts the flow of sheath fluid according to the feedback signal;

wherein the sample flow monitoring unit is a pressure sensor, which is nearby the flow cell and capable of monitoring a pressure of the flow cell; the quantitative unit increases the flow of the sheath fluid when the pressure sensor monitors that the pressure of the flow cell increases, and decreases the flow of the sheath fluid when the pressure sensor monitors that the pressure of the flow cell decreases;

or the sample flow monitoring unit is a flow sensor, which is set on a pipeline between the sample providing unit and the flow cell and is capable of monitoring the flow of the sample fluid; the quantitative unit increases the flow of the sheath fluid when the flow sensor monitors that the flow of the sample fluid increases, and decreases the flow of the sheath fluid when the flow sensor monitors that the flow of the sample fluid decreases.

6. The fluidic system according to claim 5, wherein the negative pressure source further connects to the waste container and provides a negative pressure to cause the waste fluid to flow from the flow cell to the waste container, and the negative pressure of the flow cell relative to the sample providing unit is maintained after the negative pressure provided by the negative pressure source counteracts a pressure loss which is formed when the waste fluid flows out of the flow cell.

7. The fluidic system according to claim 5, wherein the fluidic system further comprises a pulse eliminator for reducing or eliminating pressure fluctuation, the pulse eliminator being set on a pipeline between the quantitative unit and the flow cell.

8. A method for flow control in a fluidic system, comprising:

providing a negative pressure for a flow cell relative to a sample providing unit so that a sample fluid is transported from the sample providing unit into the flow cell under the negative pressure;

positioning a quantitative unit on a pipeline between a sheath container and the flow cell so that a sheath fluid is transported from the sheath container to the flow cell according to a preset flow of sheath fluid;

monitoring a flow of the sample fluid transported from the sample providing unit to the flow cell and outputting a first feedback signal reflecting flow changes of the sample fluid in real-time; and/or monitoring a pressure of the flow cell and outputting a second feedback signal reflecting pressure changes of the flow cell in real-time; and maintaining the flow of the sample fluid to be substantially constant by adjusting a flow of the sheath fluid through the quantitative unit according to the first and/or the second feedback signal(s);

wherein the flow of the sheath fluid is increased when the pressure of the flow cell and/or the flow of the sample fluid increase(s), and the flow of the sheath fluid is decreased when the pressure of the flow cell and/or the flow of the sample fluid decrease(s).

* * * * *